United States Patent [19]

Besecke et al.

[11] Patent Number: 5,442,109
[45] Date of Patent: Aug. 15, 1995

[54] PREPARATION OF OXADIMETHACRYLIC ACID

[75] Inventors: Siegmund Besecke, Hameln; Harald Lauke, Mannheim; Andreas Deckers, Ludwigshafen, all of Germany

[73] Assignee: BASF Aktiengesellschaft, Ludwigshafen, Germany

[21] Appl. No.: 297,410

[22] Filed: Aug. 29, 1994

Related U.S. Application Data

[63] Continuation of Ser. No. 996,397, Dec. 23, 1992, abandoned.

[30] Foreign Application Priority Data

Dec. 24, 1991 [DE] Germany .................. 41 42 913.3

[51] Int. Cl.$^6$ ............................................. C07C 59/42
[52] U.S. Cl. ................................ 562/583; 562/580; 560/181
[58] Field of Search ............... 562/583, 580; 560/181

[56] References Cited

U.S. PATENT DOCUMENTS 4,889,948 12/1989 Mathias et al. ................. 560/181

OTHER PUBLICATIONS

Noller, *Chemistry of Organic Compounds*, 2nd Ed., W. B. Saunders Co., Philadelphia, Pa., pp. 170–171, (1957).
Mathias et al., *Journal of Polymer Science*, Polymer Letters Edt., vol. 25, 1987, pp. 451–453.

*Primary Examiner*—José G. Dees
*Assistant Examiner*—Samuel Barts
*Attorney, Agent, or Firm*—Keil & Weinkauf

[57] ABSTRACT

At least 99% pure 2,2'[oxybis (methylene)]bis-2-propenoic acid $$CH_2=C(COOH)CH_2-O-CH_2C(COOH)=CH_2$$

is prepared by hydrolyzing an ester thereof in an aqueous basic medium and then acidifying the resultant salt.

6 Claims, No Drawings

PREPARATION OF OXADIMETHACRYLIC ACID

This application is a continuation of application Ser. No. 07/996,397, filed on Dec. 23, 1992 now abandoned.

The present invention relates to an improved process for preparing 2,2′-[oxybis(methylene)]bis-2-propenoic acid

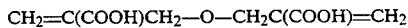

in a purity of at least 99% by hydrolysis of its esters in an aqueous medium and subsequent acidification of the resultant salt.

Oxadimethacrylic compounds of the general formula I

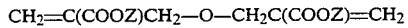

where Z is hydrogen, methyl, ethyl, n-butyl, isobutyl, tert-butyl, neopentyl, benzyl, phenethyl, trimethylcyclohexyl or tetrahydrofurfuryl, are known from U.S. Pat. No. 4,889,948, from Polymer Preprints, American Chemical Society, Division of Polymer Chemistry 31(1) (1990) 503 and from the references cited therein.

Owing to their bifunctionality they are widely used as building blocks, for example as monomers for preparing homopolymers or as comonomers or crosslinkers. However, at present only a few of them are available in adequate amounts. A further disadvantage is the usually inadequate purity of these compounds. For instance, there are differences in the reported properties of these compounds such as the melting point of 2,2′-[oxybis(methylene)]bis-2-propenoic acid (see U.S. Pat. No. 4,889,948 and Polym. Lett., 25 (1987) 451).

2,2′-[Oxybis(methylene)]bis-2-propenoic acid (oxadimethacrylic acid) can be prepared according to Example X of U.S. Pat. No. 4,889,948 by base-catalyzed hydrolysis in an aqueous methanol solution and subsequent acidification of the salt together with an unknown amount of the corresponding homopolymer. Furthermore, the polymerization of this impure oxadimethacrylic acid results in rubbery, crosslinked polymers that are virtually impossible to process any further.

It is an object of the present invention to provide a process for preparing pure oxadimethacrylic acid.

We have found that this object is achieved by an improved process for preparing 2,2′-[oxybis(methylene)]bis-2-propenoic acid

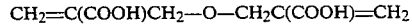

in a purity of at least 99% by hydrolysis of its esters in an aqueous medium and subsequent acidification of the resultant salt, which comprises carrying out the hydrolysis in an aqueous, basic solution.

From observations to date the success of this process is virtually independent of the nature of the starting oxadimethacrylic esters of the general formula I

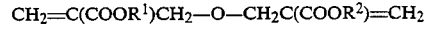

so that the ester radicals $R^1$ and $R^2$ are basically freely choosable, since they will be split off in any event. Preferred meanings for $R^1$ and $R^2$, which can be identical or different as long as they are not both hydrogen at one and the same time, are:

Hydrogen;

$C_1$–$C_{18}$-alkyl, of which preferably $C_1$–$C_{12}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl and stearyl, particularly preferably $C_1$–$C_4$-alkyl such as methyl, ethyl, n-propyl, isopropyl, n-butyl, isobutyl, sec-butyl and tert-butyl;

$C_3$–$C_8$-cycloalkyl such as cyclopropyl, cyclopentyl, cyclohexyl, cycloheptyl, cyclooctyl, 4-methylcyclohexyl, 4-methoxycyclohexyl and 2,4,6-trimethylcyclohexyl;

$C_3$–$C_8$-cycloalkyl-$C_1$–$C_5$-alkyl such as cyclopropylmethyl, cyclopentylmethyl, cyclohexylmethyl, cyclopropylethyl, cyclopentylethyl, cyclohexylethyl, cyclopropylpropyl, cyclopentylpropyl, cyclohexylpropyl, cyclopentylbutyl, cyclohexylbutyl, cyclopentylpentyl, cyclohexylpentyl, cyclooctylpentyl;

hydroxy-$C_1$–$C_5$-alkyl such as hydroxymethyl, 2-hydroxyethyl, 2-hydroxypropyl, 3-hydroxypropyl, 4-hydroxybutyl, 5-hydroxypentyl, 2,2-dimethyl-3-hydroxypropyl;

amino-$C_1$–$C_5$-alkyl such as aminomethyl, 2-aminoethyl, 3-aminopropyl, 4-aminobutyl, 5-aminopentyl;

N—$C_1$–$C_4$-alkyl-amino-$C_1$–$C_5$-alkyl such as N-methylaminomethyl, 2-(N-methylamino)ethyl, 3-(N-methylamino)propyl, 4-(N-methylamino)butyl, 5-(N-methylamino)pentyl, N-ethylaminomethyl, N-n-propylaminomethyl, N-n-butylaminomethyl;

N,N-di($C_1$–$C_4$-alkyl)amino-$C_1$–$C_5$-alkyl such as N,N-dimethylaminomethyl, 2-(N,N-dimethylamino)ethyl, 3-(N,N-dimethylamino)propyl, 4-(N,N-dimethylamino)butyl, 5-(N,N-dimethylamino)pentyl, N,N-diethylaminomethyl, N,N-di(n-propyl)aminomethyl, N,N-di(i-propyl)aminomethyl, N,N-di(n-butyl) aminomethyl, N-ethyl-N-methylaminomethyl, N-methyl-N-propylaminomethyl;

$C_6$–$C_{18}$-aryl such as phenyl, naphthyl, anthracenyl, phenanthrenyl, azulenyl, biphenylenyl, triphenylenyl, preferably phenyl, which aryl radicals may carry up to three of the groups mentioned under $R^3$;

$C_6$–$C_{18}$-aryl-$C_1$–$C_4$-alkyl, preferably phenyl-$C_1$–$C_4$-alkyl such as benzyl, 2-phenylethyl, 3-phenylpropyl, 4-phenylbutyl, particularly preferably benzyl, 2-phenylethyl, 3-phenylpropyl, in which the aryl groups may carry up to three of the groups mentioned under $R^3$;

$R^3$ is halogen such as fluorine, chlorine, bromine or iodine, $C_1$–$C_{22}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl and n-heneicosyl and n-docosyl, preferably $C_1$–$C_{12}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl and stearyl, particularly preferably $C_1$–$C_4$-alkyl such as methyl, ethyl, n-propyl, isopropyl, n-butyl, isobutyl, sec-butyl, tert-butyl; $C_1$–$C_4$-alkoxy such as methoxy, ethoxy, n-propoxy and n-butoxy, carboxyl, $C_1$–$C_4$-alkoxycarbonyl such as methoxycarbonyl, ethoxycarbonyl, n-propoxycarbonyl and n-butoxycarbonyl, aminocarbonyl, $C_1$–$C_4$-alkylaminocarbonyl such as methylaminocarbonyl, ethylaminocarbonyl, n-propylaminocarbonyl and n-butylaminocarbonyl, di ($C_1$–$C_4$-alkyl)aminocarbonyl such as dimethylaminocarbonyl, diethylaminocarbonyl, di(n-propyl)aminocarbonyl and di(n-butyl)aminocarbonyl, nitrilo, nitro, amino, $C_1$–$C_4$-alkylamino such as methylamino, ethylamino, n-propylamino and n-butylamino, di($C_1$–$C_4$-alkyl)amino such as dimethylamino, diethylamino, di(n-propyl)amino and di(n-butyl)amino.

Particularly preferred compounds are the di-$C_1$–$C_4$-alkyl esters such as the dimethyl, diethyl, dipropyl and dibutyl esters of oxadimethacrylic acid, in particular the dimethyl ester, dimethyl 2,2'-[oxybis(methylene)]bis-2-propenoate, but also their mixed esters such as the ethyl methyl ester, and also mixtures thereof.

In the process of the invention, oxadimethacrylic acid is prepared by hydrolyzing the oxadimethacrylic ester I, or a mixture of different esters of this acid, in a basic solution and then acidifying the resultant salt. Then the precipitated acid can be separated off and if necessary recrystallized in an acid, aqueous medium.

The basic solution used will in general be an aqueous solution of an alkali metal alkoxide such as sodium methoxide, potassium methoxide, sodium ethoxide, potassium ethoxide, preferably sodium methoxide, an alkali or alkaline earth metal hydroxide such as lithium hydroxide, sodium hydroxide, potassium hydroxide, magnesium hydroxide, calcium hydroxide or barium hydroxide, preferably sodium hydroxide or potassium hydroxide, or ammonia.

The reaction medium may include additives such as solubilizers and polymerization inhibitors. Suitable solubilizers are for example alcohols, preferably $C_1$–$C_4$-alcohols such as methanol, ethanol, n-propanol, isopropanol, n-butanol and tert-butanol, particularly preferably methanol and ethanol. Preferred polymerization inhibitors are the customary water-soluble compounds such as hydroquinone, hydroquinone monoethyl ether and cupric salts.

The free acid is obtained by adding to the reaction medium an acid, preferably a mineral acid such as sulfuric acid, hydrochloric acid, phosphoric acid or nitric acid, particularly preferably hydrochloric acid.

The molar ratio of base to ester will in general be selected within the range from 1:1 to 5:1, preferably from 2:1 to 4:1. The base will in general be used in the form of an aqueous solution in concentrations of from 0.1 to 40, preferably from 1 to 20, % by weight, based on water.

The amount of solubilizer will in general be within the range from 0 to 30, preferably from 0 to 10% by weight, and the amount of polymerization inhibitor within the range from 0 to 0.1, preferably from 0 to 0.5, each percentage being based on the total amount of the reaction mixture.

The amount of acid precipitant used depends on the strength and concentration of the acid. In general, the amount chosen will be such that the salt-containing medium, in general the reaction mixture, is adjusted to a pH within the range from 0.5 to 2.0, preferably from 0.5 to 1.5.

The choice of temperature is not critical, judging by experience to date. In general, the temperature range employed will extend from 10° to 100° C. under a pressure within the range from 70 to 300 kPa. It is also possible to carry out the hydrolysis in a pressure reactor at temperatures above 100° C., but in general not higher than 200° C. However, it is preferable to hydrolyze at from 15° to 50° C. under atmospheric pressure.

The precipitated oxadimethacrylic acid can be separated off by the usual methods such as filtration, decanting or centrifuging and, if desired, purified, for example by washing with cold water and then drying. From experience to date the oxadimethacrylic acid thus obtained is at least 99% pure.

Particularly pure oxadimethacrylic acid, for example with a by-product content of less than 100 ppm, is preferably obtainable by recrystallization. For this the oxadimethacrylic acid is in general dissolved in hot water at from 50° to 100° C., preferably at from 60° to 100° C., particularly preferably at from 80° to 100° C., and then crystallized out at from 5° to 30° C., preferably at from 10° to 25° C. Polymerization inhibitors such as hydroquinone monomethyl ether can be added to the solution in amounts of 10 to 20 ppm. The solution can also be treated with adsorbents such as activated carbon, kieselguhr and zeolites, then filtered hot and thereafter cooled down to bring about crystallization.

The carboxylic acid groups of oxadimethacrylic acid can be further functionalized in a conventional manner to ester, amide and ketone groups (see Houben-Weyl, Methoden der organischen Chemie, volume VIII/III, Thieme, Berlin, 1952, p. 503 ff and p. 647 ff).

Furthermore, oxadimethacrylic acid can be polymerized by conventional methods of polymerization (see U.S. Pat No. 4,889,948).

Using the process of the invention it is possible to prepare 2,2'-[oxybis(methylene)]bis-2-propenoic acid in very pure form. Oxadimethacrylic acid is thus available for the specific preparation of polymers or copolymers. Furthermore, the acid can be converted in a conventional manner, for example by reaction with alcohols or acid chlorides, into other oxadimethacrylates such as the corresponding monoesters or mixed esters and also other diesters which are otherwise obtainable only in poor yields, if at all.

EXAMPLE

Preparation of 2,2'-[oxybis(methylene)]bis-2-propenoic acid

To a solution of 15 g of sodium hydroxide in 135 g of water was added a mixture of 30 g (0.14 mol) of dimethyl 2,2'-[oxybis(methylene)]bis-2-propenoate and 60 mg of hydroquinone, which was followed by stirring at room temperature for 19 h. The reaction mixture was then brought to pH 1 with concentrated hydrochloric acid. The precipitated acid was filtered off, dissolved in 160 g of distilled water at 90° C., admixed with 10 g of active charcoal and then filtered hot. Cooling down to room temperature yielded 24.5 g (94%) of very pure 2,2'-[oxybis(methylene)]bis-2-propenoic acid having a melting point of 177° C.

By-product content: <40 ppm, determined by GC/MS measurements.

$^1$H—NMR data:=$CH_2$ 5.6 and 5.95 ppm —$CH_2$—4.25 ppm

We claim:

1. In a process for preparing 2,2'-(oxybis(methylene))1-bis-2-propenoic acid

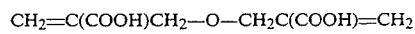

$CH_2=C(COOH)CH_2-O-CH_2C(COOH)=CH_2$ by hydrolysis of its esters in an aqueous medium and subsequent acidification of the resultant salt, the improvement which comprises carrying out the hydrolysis in an aqueous, basic solution in the presence of a polymerization inhibitor of up to 0.5% by weight based on the total amount of the reaction mixture whereby 2,2'(oxybis(methylene))1-bis-2-propenoic acid is obtained in a purity of at least 99%.

2. A process as defined in claim 1, wherein the base used comprises one or more compounds selected from the group consisting of alkali metal $C_1$–$C_3$-alkoxides, oxides or hydroxides of alkali or alkaline earth metals, and ammonia.

3. A process as defined in claim 1, wherein the esters used of 2,2'-[oxybis(methylene)]bis-2-propenoic acid are one or more di($C_1$–$C_4$-alkyl) esters.

4. A process as defined in claim 1, wherein the crude product is recrystallized.

5. In a process for preparing 2,2'-(oxybis(methylene))1-bis-2-propenoic acid $$CH_2=C(COOH)CH_2-O-CH_2C(COOH)=C_2$$

by hydrolysis of its esters in an aqueous medium and subsequent acidification of the resultant salt yielding the corresponding acid, the improvement which comprises carrying out the hydrolysis in an aqueous, basic solution in the presence of a polymerization inhibitor of up to 0.5% by weight based on the total amount of the reaction mixture and dissolving the acid obtained after acidification in hot water at from 50° to 100° C. and cooling down to bring about crystallization at from 5° to 30° C. whereby 2,2'-(oxybis(methylene))1-bis-2-propenoic acid is obtained in a purity of at least 99%.

6. In a process for preparing 2,2'-(oxybis(methylene))1-bis-2-propenoic acid $$CH_2=C(COOH)CH_2-O-CH_2C(COOH)=CH_2$$

by hydrolysis of its esters in an aqueous medium and subsequent acidification of the resultant salt yielding the corresponding acid, the improvement which comprises carrying out the hydrolysis in an aqueous, basic solution in the presence of a polymerization inhibitor of up to 0.5% by weight based on the total amount of the reaction mixture, dissolving the acid obtained after acidification in hot water at from 50° to 100° C., adding ad adsorbent, then filtering hot and thereafter cooling down to bring about crystallization at from 5° to 30° C. whereby 2,2'-(oxybis(methylene))1-bis-2-propenoic acid is obtained in a purity of at least 99%.

* * * * *

UNITED STATES PATENT AND TRADEMARK OFFICE
CERTIFICATE OF CORRECTION

PATENT NO. : 5,442,109

DATED : August 15, 1995

INVENTOR(S) : BESECKE et al.

It is certified that error appears in the above-indentified patent and that said Letters Patent is hereby corrected as shown below:

Column 5, claim 5, line 23, "$C_2$" at the end of the formula should be --$CH_2$--.

Signed and Sealed this

Thirty-first Day of October 1995

Attest:

BRUCE LEHMAN

Attesting Officer    Commissioner of Patents and Trademarks